Figure 1:
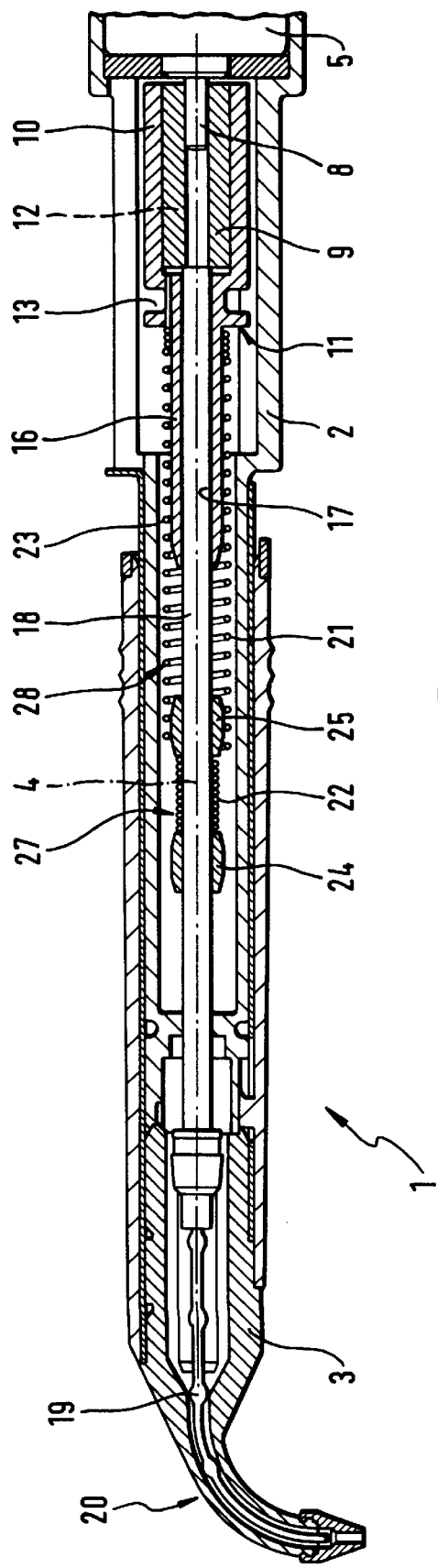

United States Patent
Boland et al.

[11] Patent Number: 6,050,818
[45] Date of Patent: Apr. 18, 2000

[54] ELECTRICALLY POWERED DENTAL CLEANSING APPARATUS

[75] Inventors: Bernhard Boland, Frankfurt; Werner Haczek, Idstein, both of Germany

[73] Assignee: Braun Aktiengesellschaft, Germany

[21] Appl. No.: 08/760,580

[22] Filed: Dec. 4, 1996

Related U.S. Application Data

[63] Continuation of application No. PCT/EP96/01097, Mar. 14, 1996.

[30] Foreign Application Priority Data

Apr. 21, 1995 [DE] Germany .......................... 195 14 710

[51] Int. Cl.$^7$ ................ A61C 1/07; A61C 3/03
[52] U.S. Cl. ..................... 433/118; 433/121; 132/322
[58] Field of Search ..................... 132/322, 323, 132/329; 433/118, 119, 121, 122, 81, 112; 601/139, 142, 143

[56] References Cited

U.S. PATENT DOCUMENTS

| | | | |
|---|---|---|---|
| 650,088 | 5/1900 | Hoag | 433/121 |
| 691,753 | 1/1902 | Dean | 433/112 X |
| 745,722 | 12/1903 | Freeman | 433/112 X |
| 2,598,624 | 5/1952 | Van Der Woude | 433/121 |
| 2,916,752 | 12/1959 | Baker . | |
| 3,927,434 | 12/1975 | Burgess . | |
| 4,060,870 | 12/1977 | Cannarella | 433/112 X |
| 4,185,474 | 1/1980 | Kulischenko | 433/112 X |
| 4,377,877 | 3/1983 | O'Rourke . | |
| 4,638,520 | 1/1987 | Eickmann . | |
| 4,954,082 | 9/1990 | Weissman | 433/118 |
| 4,995,131 | 2/1991 | Takeda . | |
| 4,995,403 | 2/1991 | Beckman et al. | 433/118 |
| 5,062,796 | 11/1991 | Rosenberg . | |
| 5,169,312 | 12/1992 | Berlin | 433/112 X |
| 5,529,495 | 6/1996 | Edwards | 433/112 |

FOREIGN PATENT DOCUMENTS

| | | | |
|---|---|---|---|
| 0 636 350 | 2/1995 | European Pat. Off. . | |
| 43 09 078 | 9/1994 | Germany . | |
| U 94 14 250 | 11/1994 | Germany . | |
| 06123343 | 5/1994 | Japan . | |
| 94004093 | 3/1994 | WIPO | 132/322 |
| 95002375 | 1/1995 | WIPO | 132/322 |

*Primary Examiner*—Nicholas D. Lucchesi
*Attorney, Agent, or Firm*—Fish & Richardson P.C.

[57] ABSTRACT

An electrically powered dental cleansing apparatus in which a cleansing implement is coupled to a drive sleeve and adapted to be rotated about a longitudinal axis. The coupling is effected by a resilient member, in particular a spring which includes a slip coupling and/or a buffer zone. Under normal conditions, the slip coupling provides a non-rotative connection between the drive sleeve and the cleansing implement. However, in the event of the cleansing implement seizing in an interproximal space, for example, the slip coupling will slip, thus avoiding potential damage. The buffer zone acts to prevent displacement of the cleansing implement—although intended by the user—in cases where, for example, the cleansing implement is positioned against a tooth surface rather than against an interproximal space.

14 Claims, 3 Drawing Sheets

ELECTRICALLY POWERED DENTAL CLEANSING APPARATUS

This is a continuation of International Patent Application PCT/EP96/01097, filed Mar. 14, 1996.

This invention relates to an electrically powered dental cleansing apparatus.

A dental cleansing apparatus of this type is known from German Offenlegungsschrift DE 43 09 078 A1 which is hereby incorporated in the disclosure content of the present patent application by express reference.

In this specification, a dental cleansing apparatus is described in which an attachment can be mounted on a handle portion. The attachment accommodates slidably therein an elongate, thin and flexible cleansing implement suitable for dental cleansing, in particular of the interproximal spaces. A switch is provided on the handle portion to enable the dental cleansing apparatus to be turned on and off. When a user displaces the switch against the force of a spring in the direction of the attachment, rotation or oscillation in alternate directions is imparted to the cleansing implement about a longitudinal axis. The displacement action further causes the cleansing implement to be moved out of the attachment. This then enables the user to clean in particular interproximal spaces by means of the rotating cleansing implement. When the user releases the switch, the force of the spring acts to return the cleansing implement into the attachment, and the motor driving the cleansing implement is turned off.

It is an object of the present invention to further improve the known dental cleansing apparatus in particular in respect of manipulation by the user and/or the service life of the cleansing implement.

To couple the cleansing implement to the driving means, provision is made in the invention for a resilient element, in particular a spring. There is thus no longer a rigid connection between the cleansing implement and the driving means, but rather, these parts are decoupled by means of a resilient or yielding connection. The resilient or yielding spring connection ensures an improved introduction of the cleansing implement into the interproximal spaces, because these can be probed automatically, so to speak, thereby avoiding improper manipulations due to, for example, inattentiveness on the user's part and/or overloading of the cleansing implement which might be otherwise provoked by the cleansing implement being wedged or seized in the interproximal area.

With the advantageous configuration of the present invention, a buffer zone is created by means of the resilient element, in particular the spring. This enables the cleansing implement and the driving means to be displaceable relative to each other. Accordingly, when the user slides the switch in the direction of the attachment, the resulting displacement travel in the buffer zone can be used up again by a compression of the spring, so that the cleansing implement itself is not displaced on encountering a resistance, for example. This has the advantage that the cleansing implement will not be moved out of the attachment when the user actuates the switch at a moment when the attachment faces a tooth surface and is thus unable to enter an interproximal space. In consequence, rather than being moved rigidly out of the attachment against the opposite tooth surface, the cleansing implement will remain in the interior of the attachment until it encounters an interproximal space which it may then enter, using, where applicable, the force of the compressed spring or the resilient element. The buffer zone of the resilient element or spring thus ensures ease of manipulation of the cleansing implement by the user. Further, the buffer zone of the spring makes a threading aid available to the user. Still further, as the cleansing implement is introduced into the interproximal space, the buffer zone acts to prevent the implement from buckling or breaking on improper handling by its user. Instead, the cleansing implement is then returned to its safe seat within the attachment against the force of the resilient element. The buffer zone thus also helps prolong the service life of the cleansing implement.

Particularly suitably, the length of the buffer zone is selected to correspond approximately to the length of travel through which the driving means are displaceable in the direction of the longitudinal axis. As a result, the cleansing implement remains within the attachment also on actuation or displacement of the switch through its entire, that is maximum, displacement travel, thus reliably avoiding the possibility of personal injury.

In the advantageous configuration of the present invention, a slip coupling is provided. The option exists to arrange this slip coupling between the resilient element, that is, the spring, and the cleansing implement and/or between the resilient element, that is, the spring, and the driving means. This slip coupling has the advantage that in normal operation of the dental cleansing apparatus the rotationally fixed transmission of rotation from the driving means to the cleansing implement is ensured. However, in the event that the cleansing implement seizes in an interproximal space due to, for example, an improper manipulation by its user, or that the rotation of the cleansing implement is slowed down for any other reasons, such variations of rotation of the cleansing implement are taken up by the slip coupling. As soon as a predetermined braking torque acts on the cleansing implement, the slip coupling will slip, thus canceling the non-rotative connection between the driving means and the cleansing implement. The slip coupling thus presents a torque transmission control device. Damage to the user's teeth by a jammed and yet still rotating cleansing implement is thus reliably avoided. Equally, slippage of the slip coupling ensures that the cleansing implement cannot penetrate the user's gums and cause an injury. Only after the cleansing implement is again freely movable will the slip coupling re-establish a non-rotative connection with the driving means, enabling the user to proceed with interproximal cleaning. It will be understood that the described slip coupling of the resilient element is also suited to operate independently of the buffer zone of the resilient element, that is, omitting the buffer zone in the dental cleansing apparatus.

In the advantageous further feature of the invention, the slip coupling effect is accomplished by the turns of the spring on a shaft, with the diameter of the turns being slightly smaller than the diameter of the shaft. In normal operation of the dental cleansing apparatus, the tight wrap of the spring around the shaft provides a non-rotative connection between the spring and the shaft and thus the cleansing implement. By contrast, when the cleansing implement exerts a braking torque on the shaft, the turns of the spring will be "unwound" by the shaft such that the diameter of the turns increases slightly. As a result, the shaft slips within the increased diameter of the turns without compelling the spring to follow it in movement. Only when the braking torque is no longer present will the turns be reduced again in diameter, wrapping around the shaft tightly, as a result of which a rotationally fixed transmission of rotation from the spring to the shaft and thus to the cleansing implement is re-established. The slip coupling realized in this manner affords great ease and economy of manufacture. Moreover, the slip coupling of the present invention ensures reliable functioning for a prolonged period of operation without the risk of wear-induced malfunctions.

In a particularly suitable configuration of the present invention, both a buffer zone and a slip coupling are provided. The buffer zone is realized in that the drive sleeve is arranged to be displaceable in the direction of the longitudinal axis. As a result, the shaft and thus the cleansing implement at the one end and the drive sleeve at the other end are displaceable relative to each other. The slip coupling is realized in that the associated turns of the spring wrap tightly around the shaft, thus ensuring a non-rotative connection between the shaft and thus the cleansing implement at the one end and the spring at the other end. To transmit this rotationally fixed connection to the drive sleeve and thus to the driving means, the spring is connected with the drive sleeve in a non-rotating relationship. This configuration of the present invention constitutes an extremely simple and low-cost link between the buffer zone and the slip coupling. Both the advantages of the buffer zone and the advantages of the slip coupling set forth in the foregoing are realized solely by means of the correspondingly configured spring.

It is particularly suitable to provide the spring with two sections of different diameters. The one section, in particular the larger-diameter section, serves to provide the buffer zone, while the other section serves to provide the slip coupling.

In the further feature of the present invention, the bearing tube of the drive sleeve serves to carry the shaft in addition to receiving and supporting the spring. The bearing tube thus provides an easy way of fixedly positioning the shaft and the spring in their proper locations.

With the further feature of the present invention, the spring is fixedly secured in place by the stop means, preventing the spring from slipping up and down on the shaft. This ensures safe functioning of the dental cleansing apparatus in a straightforward and economical way.

Figure 2:
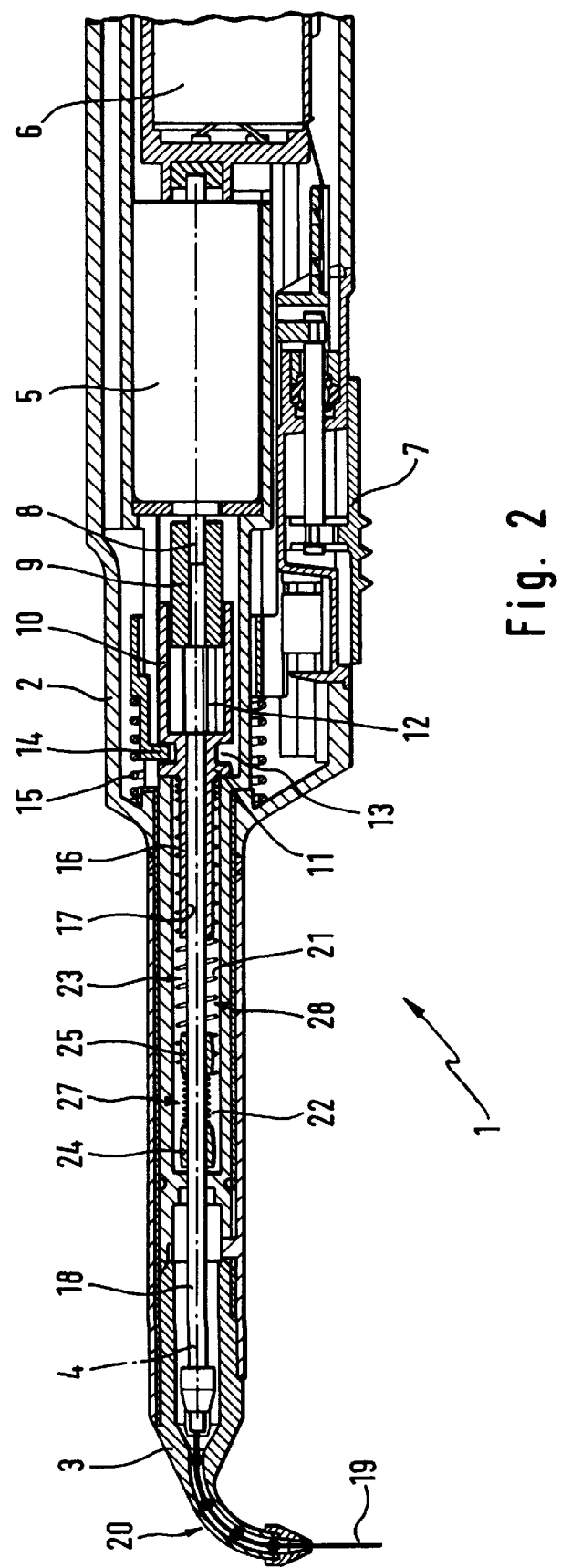
Figure 3:
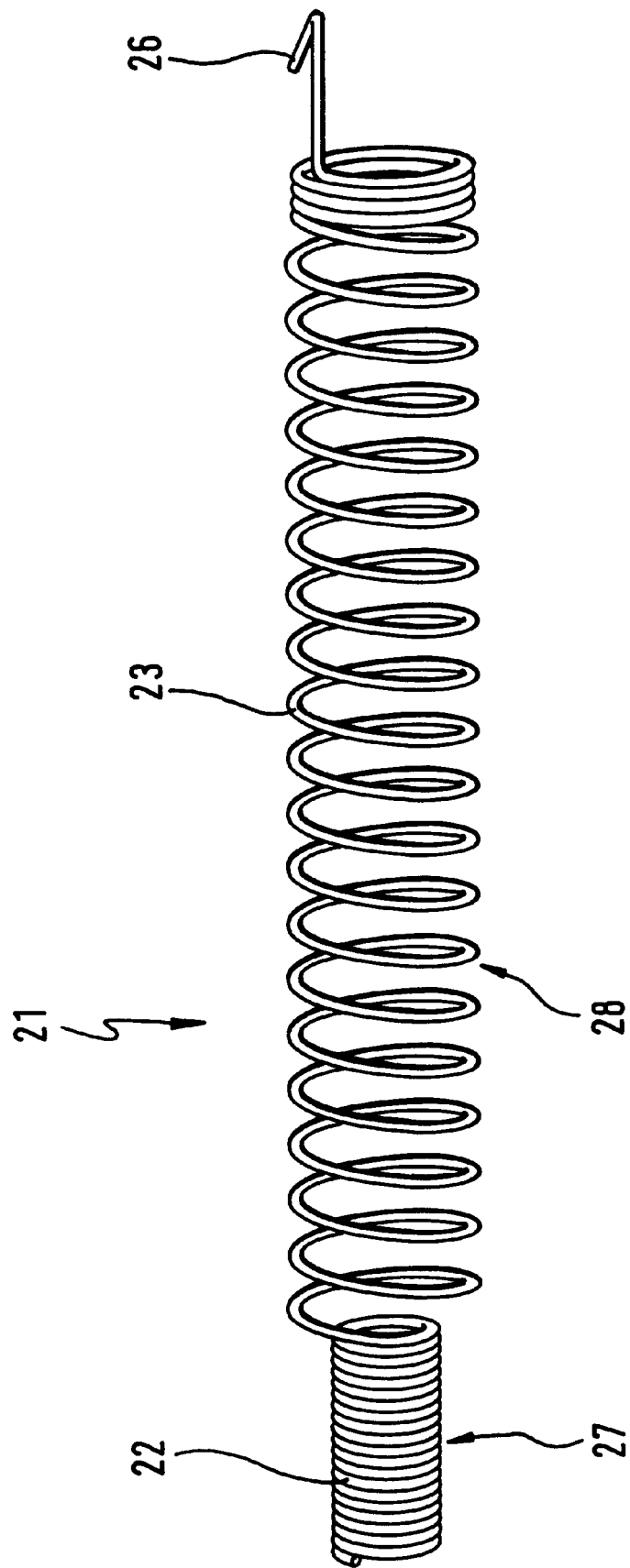

Further features, advantages and application possibilities of the present invention will become apparent from the subsequent description of embodiments illustrated in more detail in the accompanying drawings. It will be understood that any single feature and any combination of single features described and/or represented by illustration form the subject-matter of the present invention, irrespective of their summary in the claims and their back-reference. In the drawings, FIG. 1 is a schematic longitudinal sectional view of an embodiment of a dental cleansing apparatus of the present invention in an off-position;

FIG. 2 is a schematic longitudinal sectional view of the dental cleansing apparatus of FIG. 1 in an on-position; and FIG. 3 is a schematic perspective view of a spring of the dental cleansing apparatus of FIGS. 1 and 2.

German Offenlegungsschrift DE 43 09 078 A1 describes an electrically powered dental cleansing apparatus which is hereby incorporated in the disclosure content of the present patent application by express reference both in its entirety and in respect of its individual features. This known dental cleansing apparatus is the starting point for the embodiment of a dental cleansing apparatus of the present invention as described subsequently.

Referring now to FIGS. 1 and 2 of the drawings, there is shown a dental cleansing apparatus 1 which is composed of a handle portion 2 and a push-on attachment 3. The handle portion 2 and the attachment 3 are of a rod-shaped configuration extending in the direction of a longitudinal axis 4 and are conventionally circular in cross-section. Located in the interior of the handle portion 2 is an electrically powered motor 5 which is electrically connected to a source of power 6, in particular a rechargeable storage battery. By means of a switch 7 slidable in the direction of the longitudinal axis 4, the motor 5 can be turned on and off by a user.

The motor 5 includes a drive shaft 8 arranged in the longitudinal axis 4 and provided with at least one, preferably three, vane(s) 9 projecting radially outwardly and extending in the direction of the longitudinal axis 4. The vanes 9 are in engagement with a cup-shaped receptacle 10 of a drive sleeve 11, with the inside of the cup-shaped receptacle 10 being provided with longitudinal rib members 12 corresponding in number to the number of vanes 9, said rib members projecting radially inwardly and extending equally in the direction of the longitudinal axis 4. The drive shaft 8 and the drive sleeve 11 are thus connected with each other in a non-rotating relationship.

The drive sleeve 11 is accommodated in the handle portion 2 such as to be displaceable in the direction of the longitudinal axis 4. Further, the drive sleeve 11 has an annular groove 13 concentric with the longitudinal axis 4 and engaged by a ledge 14 fixedly connected with the switch 7. On displacement of the switch 7 in the direction of the longitudinal axis 4, the ledge 14 engaging the annular groove 13 causes at the same time a displacement of the drive sleeve 11 in the corresponding direction. As this occurs, the annular groove 13 makes it possible for the drive sleeve 11 to rotate about the longitudinal axis 4 in any position of the switch 7. Still further, the lengths of the vanes 9 and the longitudinal rib members 12 are selected such that the non-rotative connection between the drive shaft 8 and the drive sleeve 11 is maintained in any position of the switch 7.

Abutting against the ledge 14 is a helical spring 15 bearing against an inner wall of the handle portion 2. The helical spring 15 urges the ledge 14 and thus the switch 7 into an off-position illustrated in FIG. 1. In this off-position, the cup-shaped receptacle 10 of the drive sleeve 11 encompasses the vanes 9 of the drive shaft 8 nearly completely. The drive sleeve 11 is then in a position remote from the attachment 3. The switch 7 coupled to the drive sleeve 11 is thus equally in a position remote from the attachment 3.

When the user displaces the switch 7 along the longitudinal axis 4 in the direction of the attachment 3, the switch 7 reaches an on-position illustrated in FIG. 2. In this on-position, the vanes 9 of the drive shaft 8 are only partially in the area of the longitudinal rib members 12 of the drive sleeve 11. The drive sleeve 11 and the switch 7 are thus in a position close to the attachment 3.

When the user releases the switch 7, the helical spring 15 urges the switch 7 together with the drive sleeve 11 back into the off-position. While the motor 5 is disabled in the off-position, the motor is enabled in the on-position of the switch 7, setting the drive shaft 8 in rotation. In consequence, in the on-position also the drive sleeve 11 is set in rotation via the vanes 9 and the longitudinal rib members 12.

Extending from the drive sleeve 11 in the direction of the longitudinal axis 4 is a bearing tube 16 which is aligned with the attachment 3. The bearing tube 16 has a bore 17 concentric with the longitudinal axis 4 and receiving therein a free end of a shaft 18 with a loose fit. The shaft 18 is arranged in the longitudinal axis 4. The diameter of the shaft 18 is slightly smaller than the diameter of the bore 17, thus enabling the shaft 18 to rotate inside the bore 17 and to be displaced in the direction of the longitudinal axis 4.

The shaft 18 has its other end carried in the end of the handle portion close to the attachment 3 in a manner not shown in greater detail. At this location, an elongate, thin and flexible cleansing implement 19 is push-fitted onto the end of the shaft 18 in a non-rotating relationship in a manner equally not shown in more detail. The cleansing implement 19 is guided inside the attachment 3 which has at its free end a bight portion serving to improve manipulation by the user. In the position illustrated in FIG. 1, the cleansing implement 19 is completely retracted within the attachment 3. In the position shown in FIG. 2, the cleansing implement 19 is partially outside the attachment 3, part of its length thus extending out of the attachment 3.

Push-fitted onto the shaft 18 is a spring 21 which is illustrated in FIG. 3. The spring 21 includes a plurality of helical turns and is comprised of two sections 22, 23. In section 22, the turns are of a diameter slightly smaller than the diameter of the shaft 18, while the turns of section 23 are of a diameter slightly greater than the outside diameter of the bearing tube 16 of the drive sleeve 11. In section 22, the individual turns of the spring 21 are arranged in close proximity to each other, whilst most of the turns of section 23 are arranged at a relative spacing. In the present embodiment, section 22 of the spring 21 has about twenty turns, and section 23 has about twenty-five turns.

Section 22 of the spring 21 is push-fitted onto the shaft 18. The turns of section 22 being slightly smaller in diameter than the shaft, the spring 21 wraps tightly around the shaft 18. To prevent section 22 of the spring 21 from slipping relative to the shaft 18 in the direction of the longitudinal axis 4, a respective stop means 24, 25 is provided on the shaft 18 at either end of section 22, both of said stop means being fixedly connected with the shaft 18. Another function served by the stop means 24 and 25 is to prevent the shaft 18 from being pulled out or pushed into the handle portion 2 completely when the cleansing implement 19 is pulled off from or pushed onto the shaft 18.

The section 23 of the spring 21 adjoining the section 22 is arranged at the end of the section 22 remote from the attachment 3 and has part of it pushed onto the shaft 18, and the remainder onto the bearing tube 16. The section 23 of the spring 21 extends as far as into the area of the annular groove 13 of the drive sleeve 11 where the spring 21 is non-rotatably located on the drive sleeve 11 by means of a hook-shaped free end 26.

FIG. 1 shows the dental cleansing apparatus 1 in the off-position. The drive sleeve 11 encompasses the vanes 9 completely. The spring 21 located on the drive sleeve 11 has pulled the shaft 18 into a retracted position by means of the tight wrap of its section 22 and the stop means 25. As a result, the cleansing implement 19 pushed onto the shaft 18 occupies equally a retracted position in the interior of the attachment 3.

As mentioned in the foregoing, FIG. 2 shows the dental cleansing apparatus 1 in the on-position. In this position, only part of the drive sleeve 11 continues to be in the area of the vanes 9. By means of the tight wrap of section 22 of the spring 21 and the stop 24, the shaft 18 is in an advanced position. This causes the cleansing implement 19 to occupy equally an advanced position, protruding from the attachment 3.

As set forth in the foregoing, in the on-position shown in FIG. 2, the motor 5 sets the drive sleeve 11 in rotation about the longitudinal axis 4. As a result, the spring 21 which is fitted onto the bearing tube 16 in a non-rotating relationship thereto rotates equally about the longitudinal axis 4. Because the shaft 18 sits in the bore 17 of the bearing tube 16 with a loose fit only, this rotation cannot as yet be transmitted to the shaft 18 without further means. This means is made available by section 22 of the spring 21 which transmits the rotation also to the shaft 18. This is accomplished in that the diameter of the turns of section 22 of the spring 21 is slightly smaller than the diameter of the shaft 18, causing the shaft 18 to be encircled by the spring 21 tightly. The rotary motion thereby transmitted to the shaft 18 also sets the cleansing implement 19 in rotation which is push-fitted onto the shaft 18 in a non-rotating relationship thereto. The user is thus in a position to clean out interproximal areas using the rotating cleansing implement 19 as it projects out of the attachment 3.

Now it may happen that in the on-position described the cleansing implement 19 seizes in an interproximal space which is, for example, very narrow. To avoid damage to the user's teeth and/or destruction of the cleansing implement 19 in such an event, section 22 of the spring 21 acts as a slip coupling 27. The turns of section 22 of the spring 21 are wound onto the shaft 18 in such fashion as to be practically unwound with the spring 21 rotating and the shaft 18 not rotating, causing the diameter of the turns of section 22 of the spring 21 to become slightly larger. This enlarged diameter enables the shaft 18 to slip beneath the turns of section 22 of the spring 21. Accordingly, the rotary motion of the drive sleeve 11 stops being transmitted to the shaft 18 and the cleansing implement 19. Only when the cleansing implement 19 is dislodged and in a position to rotate again freely will the turns of section 22 of the spring 21 encircle the shaft 18 again tightly, so that the rotation of the drive sleeve 11 is transmitted via the spring 21 to the shaft 18 and on to the cleansing implement 19.

The slip coupling 27 thus provides a non-rotative connection between the drive sleeve 11 and the cleansing implement 19 provided that a predetermined braking torque on the cleansing implement 19 is not exceeded. If this particular braking torque is exceeded, meaning in the extreme case that the cleansing implement 19 is brought to an involuntary stop, the slip coupling 27 will slip, thus canceling the non-rotative connection between the drive sleeve 11 and the cleansing implement 19. By means of the slip coupling 27 it is thus possible to limit the torque to be transmitted to the cleansing implement 19. The amount at which the slip coupling starts canceling the non-rotating relationship, slipping accordingly, depends in particular on the diameter, the number and the spring constant of the turns of section 22 of the spring 21.

Unlike the embodiment described, it is also possible to provide a slip coupling in section 23 of the spring 21, in particular on the outside diameter of the bearing tube 16. In this construction, it would be necessary to connect section 22 of the spring 21 with the shaft 18 in a non-rotating relationship. Moreover, the possibility exists to provide two slip couplings, one in section 22 and the other in section 23 of the spring 21.

Another hazard of improper manipulation of the apparatus exists, for example, when the attachment 3, instead of being opposite an interproximal space on displacement of the switch 7 from the off- to the on-position, encounters the user's tooth surface. In this event, it would be possible for the cleansing implement 19 to be advanced out of the attachment 3 without further means, but it would buckle on contact with the tooth surface. In order to preclude this situation in which the user's teeth or gums could be damaged or injured and/or the cleansing implement 19 destroyed, the spring 21 includes a buffer zone 28. With the buffer zone 28 it is possible for the switch 7 and thus also the drive sleeve 11 to be displaced towards the on-position without this involving at the same time a displacement of the shaft 18 and thus of the cleansing implement 19. The drive sleeve 11 and the cleansing implement 19 are thus displaceable relative to each other in the direction of the longitudinal axis 4. In the event of a non-displaceable or blocked condition of the cleansing implement 19, the displacement of the drive sleeve 11 towards the on-position thus occurs against the pressure of the turns of section 23 of the spring 21. When blockage of the cleansing implement 19 is released, the compressed spring 21 operates to advance the cleansing implement 19 out of the attachment into the on-position.

The length of the buffer zone 28 in the direction of the longitudinal axis 4 is selected such as to correspond at least to the length of travel through which the drive sleeve 11 is displaceable in the direction of the longitudinal axis 4 from the off- to the on-position. As a result, the drive sleeve 11 can be displaced completely from the off-position shown in FIG. 1 into the on-position shown in FIG. 2, without this displacement motion being transmitted to the shaft 18 and on to the cleansing implement 19. Instead, the entire displacement motion is taken up in the buffer zone 28 of the spring 21 by a relative displacement of the drive sleeve 11 and the shaft 18 while at the same time the spring 21 is compressed, until the free end of the bearing tube 16 of the drive sleeve 11 abuts the stop means 25 of the shaft 18.

The complete drive sleeve 11 is preferably integrally made of a plastic material. The shaft 18 is equally made of plastic, which enables the stop means 24, 25 to be fastened to the shaft 18 by induction welding. The spring 21 is bent from a length of spring wire in accordance with FIG. 3.

We claim:

1. An electrically powered dental cleansing apparatus comprising:
    a driver having a drive shaft;
    a cleansing implement having a central axis, said coupling element coupled to said drive shaft and adapted to be rotated about its central axis; and
    a resilient element coupling the cleansing implement to the drive shaft, said resilient element including a buffer zone enabling the cleansing element to be displaceable relative to the driver in the direction of the central axis.

2. The dental cleansing apparatus as claimed in claim 1, wherein at least portions of the driver are displaceably arranged in the dental cleansing apparatus, and the buffer zone has a length corresponding approximately to the length of travel through which the driver is displaceable in the direction of the central axis.

3. The dental cleaning apparatus as claimed in claim 1, wherein the resilient member is a spring having a multiplicity of helical turns.

4. The dental cleansing apparatus as claimed in claim 3, wherein at least one of the turns of the spring provides a slip coupling enabling the torque transmitted from the driver to the cleansing implement to be limited.

5. The dental cleansing apparatus as claimed in claim 3, wherein at least one of the turns of the spring provides a torque transmission control device enabling the torque transmitted from the driver to the cleansing implement to be limited.

6. The dental cleansing apparatus as claimed in claim 4 or 5, wherein the cleansing implement is adapted to be push-fitted onto a shaft displaceable in the direction of the central axis.

7. The dental cleansing apparatus as claimed in claim 6, wherein the turns of the spring providing the slip coupling are carried by the shaft and have a diameter smaller than the diameter of the shaft.

8. The dental cleansing apparatus as claimed in claim 6, wherein the shaft is provided with at least one stop means which position the turns of the slip coupling in their proper location relative to the shaft in the direction of the central axis.

9. The dental cleansing apparatus as claimed in claim 8, wherein the shaft is provided with two stop means.

10. The dental cleansing apparatus as claimed in claim 3, wherein the spring includes two sections of different diameters in the direction of the central axis.

11. The dental cleansing apparatus as claimed in claim 1 or 3, wherein the driver includes a drive sleeve displaceable in the direction of the central axis, and the resilient element is connected with the drive sleeve in a manner preventing relative rotation.

12. The dental cleansing apparatus as claimed in claim 11, wherein the drive sleeve includes a bearing tube arranged in the direction of the central axis, said bearing tube receiving therein the shaft with a loose fit.

13. The dental cleansing apparatus as claimed in claim 11, wherein the drive sleeve includes a bearing tube arranged in the direction of the central axis, said bearing tube receiving therein the shaft with a loose fit and said resilient element being push-fitted onto the bearing tube.

14. The dental cleansing apparatus as claimed in claim 11, wherein the drive sleeve includes a bearing tube arranged in the direction of the central axis, and said resilient element is push-fitted onto the bearing tube.

* * * * *